(12) United States Patent
Marashdeh et al.

(10) Patent No.: US 9,927,385 B2
(45) Date of Patent: Mar. 27, 2018

(54) ACTIVE CONTROL GUARDS AND RATIONOMETRIC CALIBRATION AND RECONSTRUCTION FOR USE WITH ELECTRICAL CAPACITANCE VOLUME TOMOGRAPHY

(71) Applicants: Ohio State Innovation Foundation, Columbus, OH (US); Tech4Imaging LLC, Columbus, OH (US)

(72) Inventors: Qussai Marashdeh, Columbus, OH (US); Liang-Shih Fan, Columbus, OH (US); Fernando Teixeira, Columbus, OH (US); Zeeshan Zeeshan, Columbus, OH (US)

(73) Assignees: OHIO STATE INNOVATION FOUNDATION, Columbus, OH (US); TECH4IMAGING LLC, Columbus, OH (US)

( * ) Notice: Subject to any disclaimer, the term of this patent is extended or adjusted under 35 U.S.C. 154(b) by 0 days.

(21) Appl. No.: 15/304,744

(22) PCT Filed: May 15, 2014

(86) PCT No.: PCT/US2014/038032
§ 371 (c)(1),
(2) Date: Oct. 17, 2016

(87) PCT Pub. No.: WO2015/174975
PCT Pub. Date: Nov. 19, 2015

(65) Prior Publication Data
US 2017/0038328 A1    Feb. 9, 2017

(51) Int. Cl.
G01N 27/22    (2006.01)
A61B 5/053    (2006.01)
G01F 1/74    (2006.01)
G01F 1/56    (2006.01)
A61B 5/00    (2006.01)

(52) U.S. Cl.
CPC ......... G01N 27/228 (2013.01); A61B 5/0536 (2013.01); G01F 1/56 (2013.01); G01F 1/74 (2013.01); A61B 5/4836 (2013.01); A61B 2562/0214 (2013.01)

(58) Field of Classification Search
CPC ...... G01N 27/24; G01R 27/2605; G01F 1/56; G01F 1/74; A61B 5/0536
See application file for complete search history.

(56) References Cited

U.S. PATENT DOCUMENTS 6,081,322 A    6/2000 Barbour
6,426,615 B1    7/2002 Mehta
(Continued)

OTHER PUBLICATIONS

Cao, Z. et al., Image Reconstruction Technique of Electrical Capacitance Tomography for Low-Contrast Dielectrics Using Calderon's Method, Measurement Science and Technology, 2009, pp. 1-12, vol. 20.

*Primary Examiner* — Huy Q Phan
*Assistant Examiner* — Dustin Dickinson
(74) *Attorney, Agent, or Firm* — Standley Law Group LLP

(57) ABSTRACT

A method and system for generating a three-dimensional tomograph of a vessel interior or other object using a sensor having a plurality of electrodes and active control segments that are electrically isolated from the electrodes.

29 Claims, 11 Drawing Sheets

(56) References Cited

U.S. PATENT DOCUMENTS

| | | | |
|---|---|---|---|
| 6,496,020 B1* | 12/2002 | Davey | G01N 27/221 |
| | | | 324/667 |
| 2006/0076955 A1* | 4/2006 | Saylor | G01R 33/34046 |
| | | | 324/320 |
| 2008/0053211 A1* | 3/2008 | Gamberini | G01G 7/06 |
| | | | 73/149 |
| 2010/0006441 A1 | 1/2010 | Renaud et al. | |
| 2010/0097374 A1 | 4/2010 | Fan et al. | |
| 2011/0074058 A1* | 3/2011 | Lederer | B29C 47/92 |
| | | | 264/40.7 |
| 2013/0085365 A1 | 4/2013 | Marashdeh et al. | |
| 2013/0221986 A1* | 8/2013 | Riegel | G01N 27/06 |
| | | | 324/601 |
| 2014/0063456 A1 | 3/2014 | Zhou et al. | |

\* cited by examiner

PRIOR ART

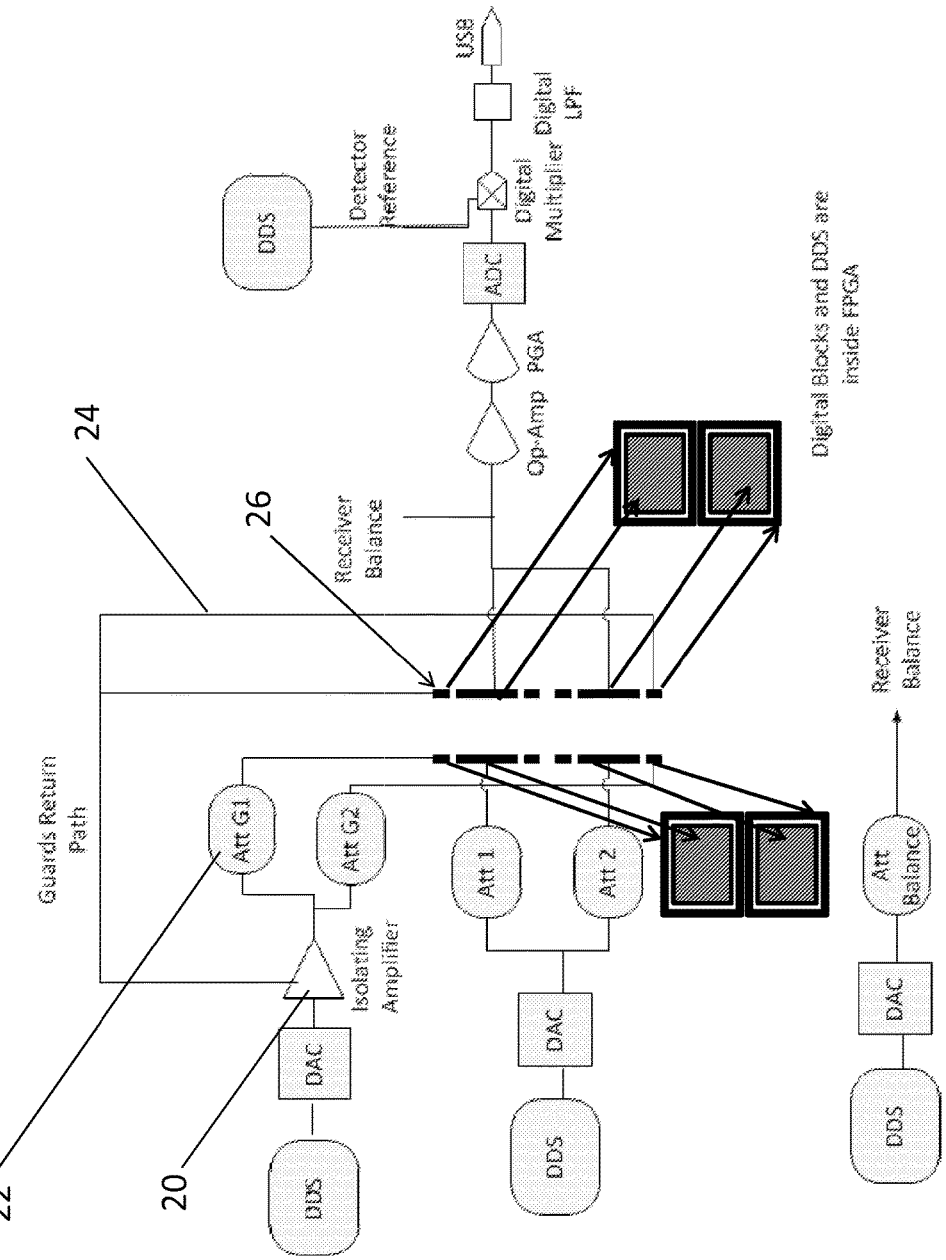
Figure 4: Guard Isolation: two sender segments and two receiver segments (Circuit Example)

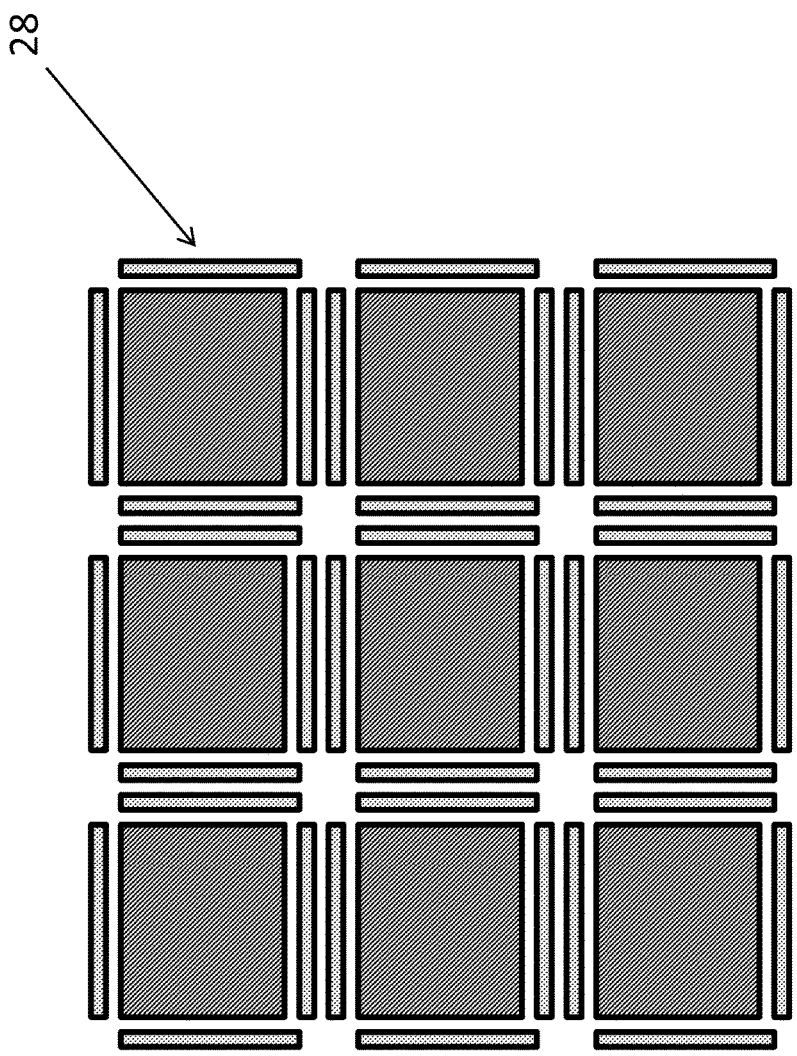
Figure 5: Active Guards: II(segmented)

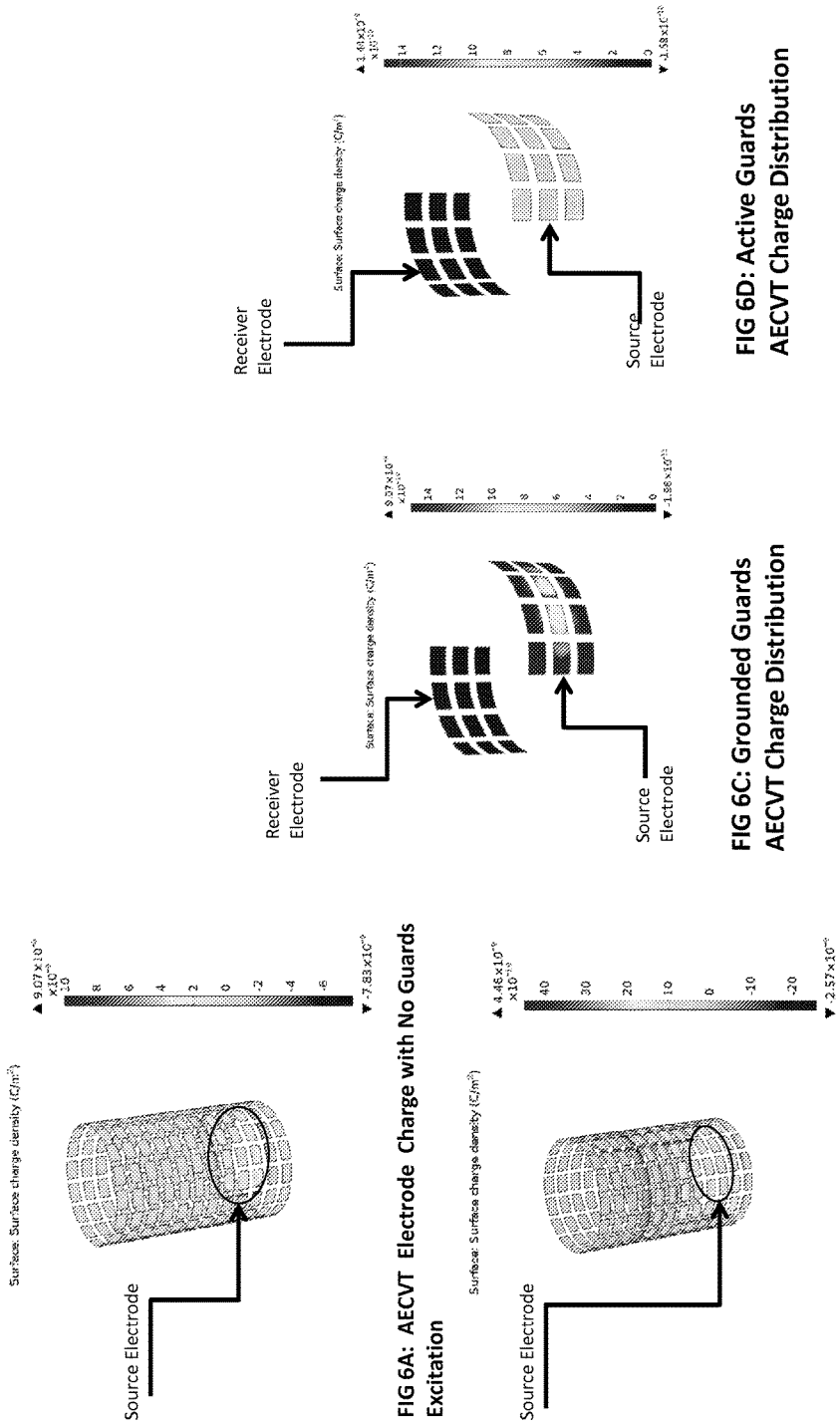

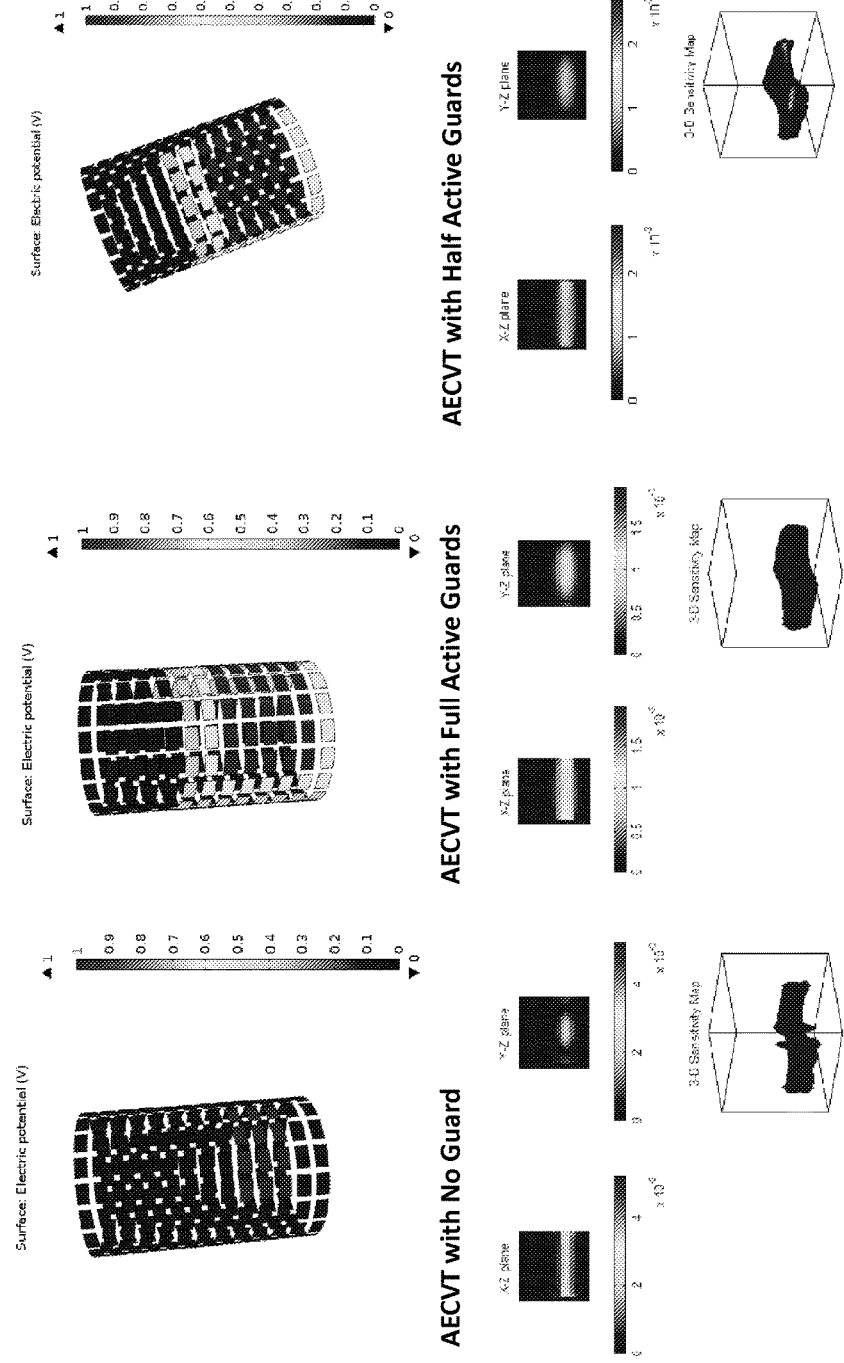
Figure 7: Sensitivity Dependence on Guard Excitation Pattern
FIG 7A: S12 Standard AECVT
FIG 7B: S12 AECVT with Active Guards I
FIG 7C: S12 AECVT with Active Guards II

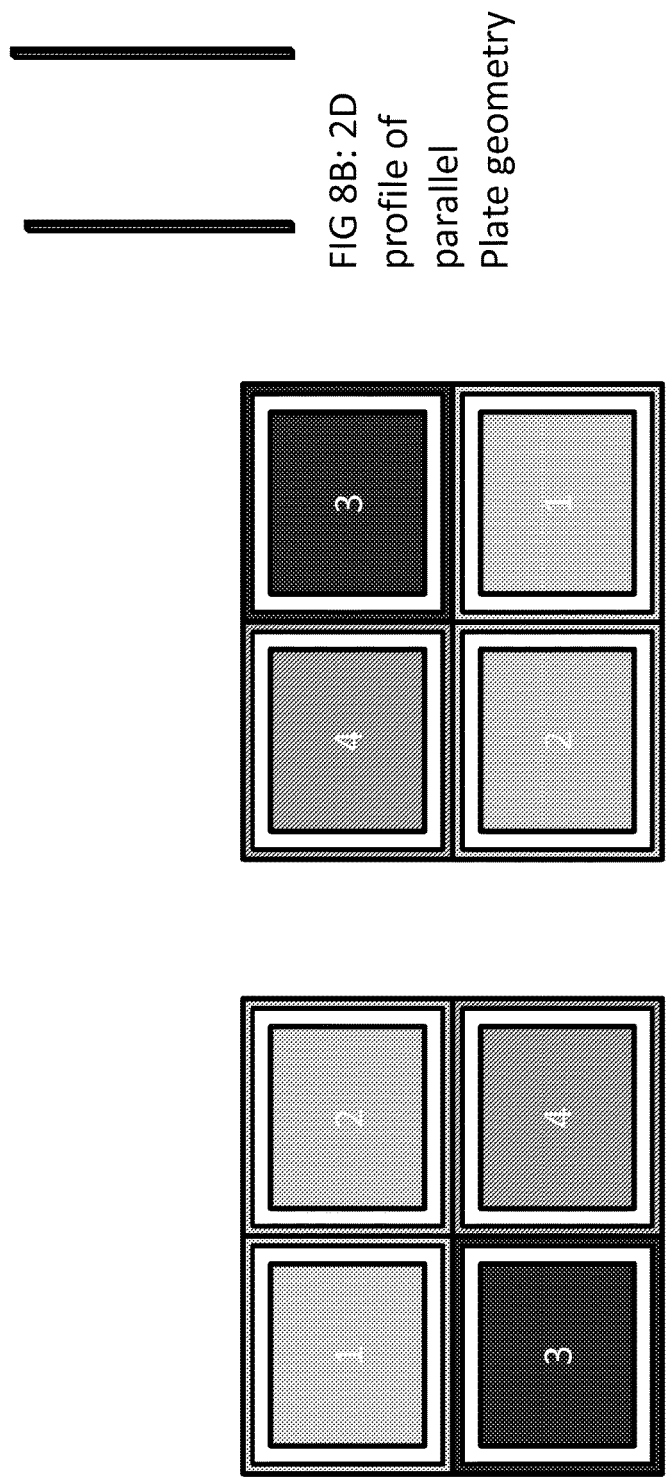

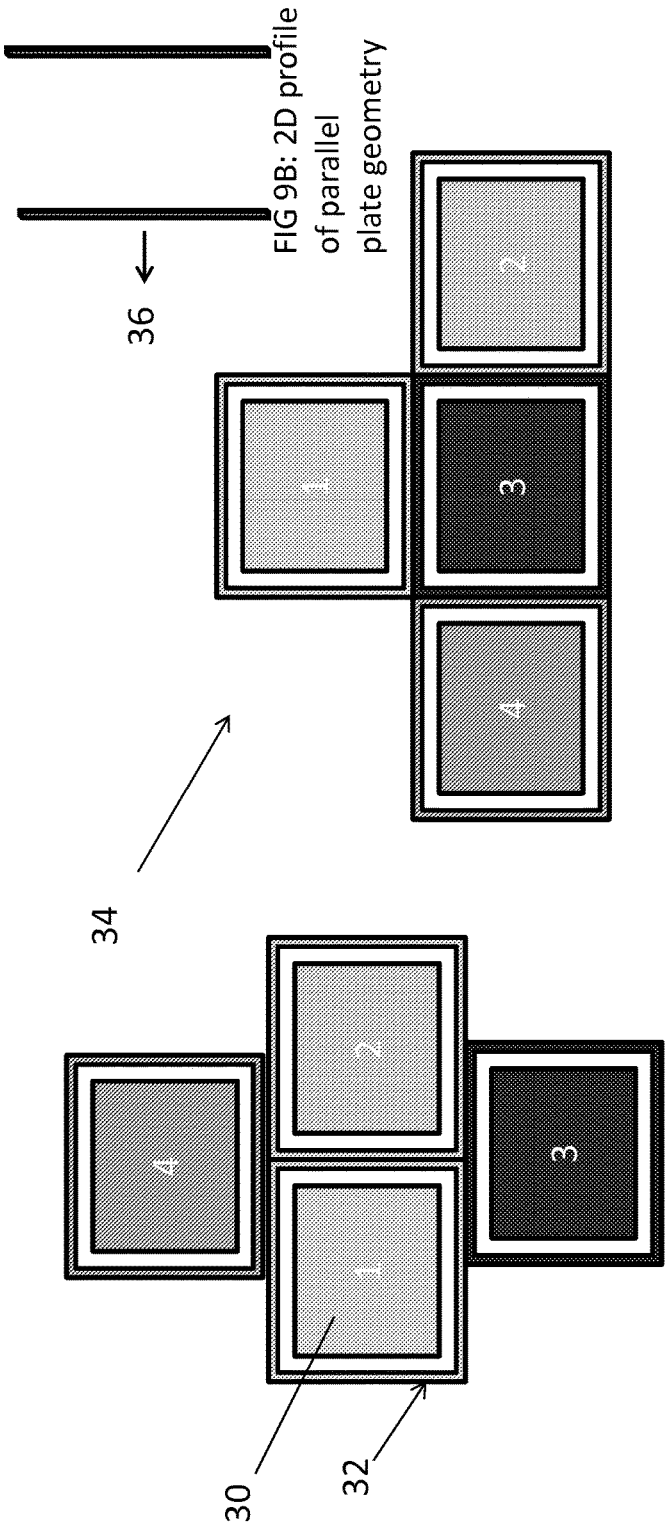

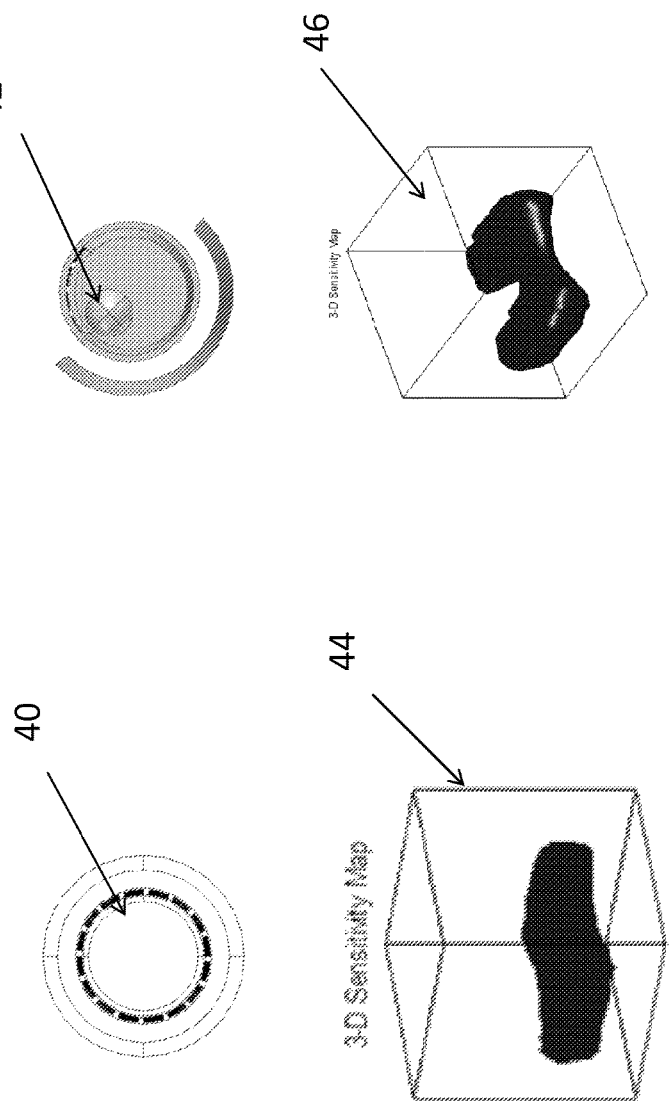
Figure 10: Focus of sensitivity distribution based on recursive method.
FIG 10A: Sensitivity map with active guards in an empty domain
FIG 10B: Sensitivity map with active guards in presence of a Phantom with low dielectric value and after reconfiguring active guards to maintain close to homogenous charge distribution on sender/receiver plates

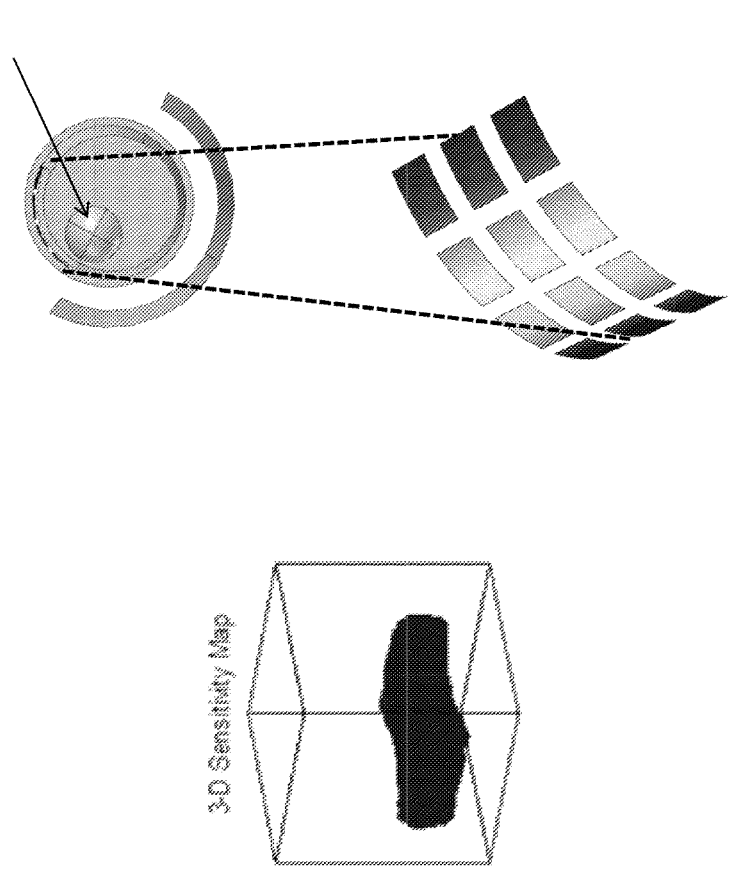

ACTIVE CONTROL GUARDS AND RATIONOMETRIC CALIBRATION AND RECONSTRUCTION FOR USE WITH ELECTRICAL CAPACITANCE VOLUME TOMOGRAPHY

BACKGROUND OF THE INVENTIVE FIELD

Electrical Capacitance Tomography (ECT) is the reconstruction of material concentrations of dielectric physical properties in the imaging domain by inversion of capacitance data acquired by a capacitance sensor. Electrical Capacitance Volume Tomography (ECVT) is the direct three-dimensional (3D) reconstruction of volume concentration or physical properties in the imaging domain utilizing 3D features in the ECVT sensor design. Adaptive ECVT is an advanced technology that introduces a new dimension into 3D sensor design by applying voltages of various frequencies, amplitudes, and phases to different capacitance plate segments. Adaptive sensors can provide a much larger number of independent capacitance measurements of the imaging volume thereby enabling better resolution for the images.

Driven and grounded guards were developed to reduce or eliminate the fringe effect present in ECT sensors. Prior guards developed thus far are not flexible enough to cope with modern applications of capacitance tomography sensors.

The present invention relates to the novel use of active control guards with the objective of controlling the charge distribution on different capacitance electrodes and hence controlling the sensor sensitivity in a predictable manner. In the preferred embodiment, active control guards are segments that are electrically isolated from the sender or receiver plates from which capacitance is being measured. The active control guards influence the charge distribution on the sender and/or receiver plates without changing the capacitance between them. A change on the charge distribution on the sender and/or receiver plates allows for controlling the sensitivity map between any such pair of plates. This control is effected through a unique design and set of features explained below.

The present invention also relates to a new method of calculating the sensitivity matrix directly from the charge distributions on the sender and receiver plates. It also relates to estimating aggregate effect of multiple active control guards, when activated together, on sender and receiver charge distribution. This aggregate effect is estimated from a weighted summation of the effect of each control guard, when activated alone, on sender and receiver plates.

The present invention also relates to rationometric reconstruction and calibration that eliminates the conventional requirement of calibration in ECT and ECVT sensors based on the use of full and empty imaging domains. In the preferred embodiment, ECVT and AECVT plates are designed to have similar or rationometric capacitance values for a homogeneous medium.

The present invention also relates to using a reference capacitor in the measuring circuit to decode the effective dielectric permittivity between plates of the rationometric sensor.

The present invention also relates to using a recursive method for reconfiguring the active control guards patterns for each pair of capacitance plates used in data acquisition. In the preferred embodiment, recursive activation uses measured capacitance to reconfigure the impressed voltages at the active control guards with a new pattern so as to counter polarization in the dielectric material to maintain as close to a linear relation as possible between sensitivity distribution and dielectric distribution when dielectric distribution in the imaging domain evolves over time. Maintaining a nearly linear relation between charge distributions on measuring plates and dielectric distribution in the imaging domain, at all times, ensures sensor sensitivity is only affected at regions where dielectric distribution has changed. This allows for higher resolution imaging as the nonlinearity of the inverse problem is mitigated and changes in the capacitance signal can be directly traced back to locations in the imaging domain that caused the recorded changes in capacitance signals.

SUMMARY OF THE EXEMPLARY EMBODIMENTS

The present invention is directed to process tomography and, in particular, to an electrical capacitance volume tomography (ECVT), adaptive electrical capacitance volume tomography (AECVT), through (1) the use of reconfigurable and active control guards that allow for influencing charge distribution on sender and/or receiver capacitive plates or capacitive segments to produce a preferred sensitivity map in the domain to be imaged, (2) calculating sensitivity maps of influenced sender and receiver plates in isolation from active control guards, (3) establishing basis functions for establishing active control guard patterns, (4) eliminating the need for capacitance normalization, (5) allowing higher resolution by applying the active control guards patterns to maintain a near, or substantially near, linear relation between sensitivity distribution and dielectric material distribution by controlling the charge distribution on sender and receiver plates regardless of the condition on the domain to be imaged, and (6) isolating inter-plate and inter-segment interference.

Dynamic ECVT is a technology that measures mutual capacitances between a set of sensor plates placed around a volume of space to generate a volumetric image of such region. ECVT technology has been applied to provide images of objects moving through a pipe, for example. ECVT has provided insights into multiphase flow phenomena in many industrial processes having a combination of gas, liquid, and solid states. These flow phenomena including pneumatic conveying, oil pipe lines, fluidized beds, bubble columns, and many other chemical and biochemical processes. ECVT can also be used for imaging biological processes and tissues. In an AECVT system a plate can be configured using a combination of a plurality of electrode segments and active control guards. The present invention is designed so that the various plate geometries can be activated using various combinations of electrode segments and active control guards.

Capacitance sensor guards were previously introduced to eliminate fringe effects in two-dimensional (2D) ECT sensors and were positioned at the top and bottom of a sender plate and activated by a voltage potential identical to the sender plate. The design of the present invention utilizes active control guards that can be positioned at different locations and with different activation levels toward targeted adjustment of sensitivity map. Moreover, the plate functionality is fully reconfigurable, that is, the same physical plate can act as a sender/receiver plate for a set of measurements and as an active control guard in another set of measurements, without the need for any change of the plate's structure or positioning.

The present invention provides an innovative design and functionality for active control guards for controlling the charge distribution on sender/receiver capacitance pairs of plates to change the sensitivity map between them while maintaining the capacitance between them unchanged. Specifically, features include an electric isolation of the active control guards from the sender/receiver capacitance pair of electrodes for avoiding a change on the mutual capacitance of said sender/receiver pair or plates; a basis function method through which active control guards can be activated with required voltage for producing a required sensitivity map; a method to calculate sensitivity map in isolation of active control guards; a method to reduce singularities (i.e. very high sensitivity gradient in a very small region in the imaging domain) in the region between adjacent plate edges; a method to reconfigure active control guards according to the conditions of the imaging domain with the objective to maintain uniform or controlled charge distribution on the sender and receiver plates; a method to consider capacitance measurements for direct reconstruction and without need for prior normalization; and a method to design ECT and ECVT sensors for rationometric reconstruction. Details of these features are described below.

The active control guard design of the present invention enables placement of electrically isolated guards around sender/receiver plates and segments on ECVT and AECVT sensors, respectively. Active control guards at each side of a plate are activated so as to repel or attract charges on the sender and receiver plates according to the relative voltage levels and positions. The combined effect of the voltage pattern used for exciting active control guards around a given sender or receiver sensor plate changes the charge distribution on the latter thereby producing a new sensitivity map. In prior technology, driven guards were used to eliminate fringe effects at edges of a 2D capacitance plate. Driven guards were applied in a way that affects measured capacitance of sensor plates. This prior technology is different than the present invention in at least four ways. First, the prior technology is not concerned with, and does not involve, controlling the sensitivity map to increase the number of independent measurements. Second, the driven guards used in prior technology were not electrically isolated, and thus, they perturbed the value of measured capacitance between sender and receiver plates. In the present invention, isolation of active control guards ensures that the capacitance value between the sensor and receiver plates does not change with different activation levels for the active control guards. Third, the present invention also provides a method to calculate the sensitivity map of the capacitance sensor in isolation of the active control guards based on the enforced charge distribution on the sender and receiver plates. Fourth, the present invention allows for generating different sensitivity maps, and hence obtaining independent measurements, from the same pair of capacitance plates by applying different active control guard patterns.

Isolation circuits also allow any plate in the ECVT or segment in the AECVT to act either as sender/receiver guard or as an active control guard interchangeably by connecting it to the proper isolation circuits. Plates or segments connected to isolation circuits are enabled as active control guards whereas plates or segments activated by regular capacitance measuring circuits are enabled as sender or receiver plates.

The active design of the present invention also preferably includes a method for calculating the sensitivity map based on enforcement of given spatial charge distributions on the sender and receiver plates. The method is based on simulating the active control guard effect on sender and receiver sensor plates for producing a given spatial charge distribution. This charge distribution is then impressed on the plates in a new simulation, and without active control guards. The electric field produced by the impressed charges in this new simulation yields the sensitivity map representation of the sensor sensitivity in the imaging domain in the presence of electrically isolated, active control guards.

The present invention also preferably includes eliminating singularities in electric field and sensitivity distributions between adjacent sensor plates by using electrically-isolated active control guards to control charge distribution on the capacitance sensor plates.

The present invention also preferably includes geometrically identical capacitance plates (e.g., for AECVT sensors plates are formed using a combination of electrode segments (e.g., electrodes) and active control guards) with varying voltage distribution on the plate segments. This arrangement eliminates the need to normalize the capacitance values after measurement. The capacitance plate geometry here refers to the physical distribution and arrangement of plates and segments for the same average voltage excitation level across segments and plates. Whereas the average excitation level is fixed, the spatial voltage distribution may vary.

The present invention also preferably includes "effective" geometrically identical capacitance plate combinations by using different voltage activation on adaptive plates that are not geometrically identical. Here, plate combinations that are not geometrically identical are converted to an "effective" identical geometry by applying activation voltages on each plate pair to yield similar effective capacitance response (i.e. similar measured current) in an imaging domain with homogenous dielectric distribution.

The present invention also preferably includes constructing basis patterns for the excitation of active control guards to yield specific charge distributions and sensitivity maps. The present invention also exploits the principle of superposition for potential voltages on active control guards. Excitation of charge distributions on sender and receiver plates are used to synthesize activation patterns that are linear combinations of established basis patterns. The sensitivity map thus produced is also the linear addition of the sensitivity maps produced by the basis patterns individually. Superposition allows analysis of the effect of the active guard's pattern of multiple guard electrodes by considering the effect of each guard alone on sender and receiver plates. The overall effect of an active guard pattern on sender and receiver plates is a linear combination of individual effects of individual guard activation. This superposition principle can also be used to design active guard activation patterns for a desired effect on sender and receiver plates.

The interactive design of the present invention includes eliminating singularities and ill-posedness between adjacent segments of varying voltage in an AECVT sensor plate by placing active control guards around each plate or plate segment to yield near homogenous charge distribution across each plate or segment.

The interactive design of the present invention also allows for the voltage pattern of the active control guards to be reconfigured so as to ensure near linear relation between sensitivity distribution and dielectric distribution in the imaging domain through the excitation of active control guards aimed at reconfiguring the charge distribution on sender and receiver plates to counter polarization charges of dielectric material in imaging domain, for any dielectric distribution in the imaging domain.

BRIEF DESCRIPTION OF THE DRAWINGS

A better understanding of an exemplary embodiment will be obtained from a reading of the following detailed description and the accompanying drawings wherein identical reference characters refer to identical parts and in which:

FIG. 4 illustrates one embodiment of a circuit of the present invention for measuring the capacitance of adaptive sensor segments for single capacitance measurements in isolation of active control guard excitation;

FIG. 5 illustrates another embodiment of an ACECVT sensor plate with each segment of the sensor plate surrounded by segments of active control guards;

FIGS. 6A-D illustrate examples of the change of charge distribution on AECVT plate segments by controlling the active control guard excitation around the plate segments;

FIGS. 7A-C illustrate examples where the sensitivity of a plate combination is changed by active control guard excitation while the capacitance value of the plate combination is maintained;

FIG. 8A illustrates an example of a 2D depiction of a parallel plate capacitance combination showing various segment and guard excitations;

FIG. 8B illustrates a 2D profile of parallel plate geometry;

FIG. 9A illustrates an example of a 2D depiction of a parallel plate capacitance combination showing various segment and guard excitations for plates of different geometry;

FIG. 9B illustrates a 2D profile of parallel plate geometry;

FIG. 10A illustrates an example of a sensitivity map for a homogenous domain;

FIG. 10B illustrates an example of a sensitivity map of a domain with a phantom;

FIG. 11A illustrates an example of a uniform sensitivity distribution map of an empty domain using active control guards;

FIG. 11B illustrates an example of a highly polarizing phantom in the imaging domain and associated charge distribution;

FIG. 11C illustrates an example of the sensitivity map after activation of active control guards.

DETAILED DESCRIPTION OF THE PREFERRED EMBODIMENTS

Figure 1:
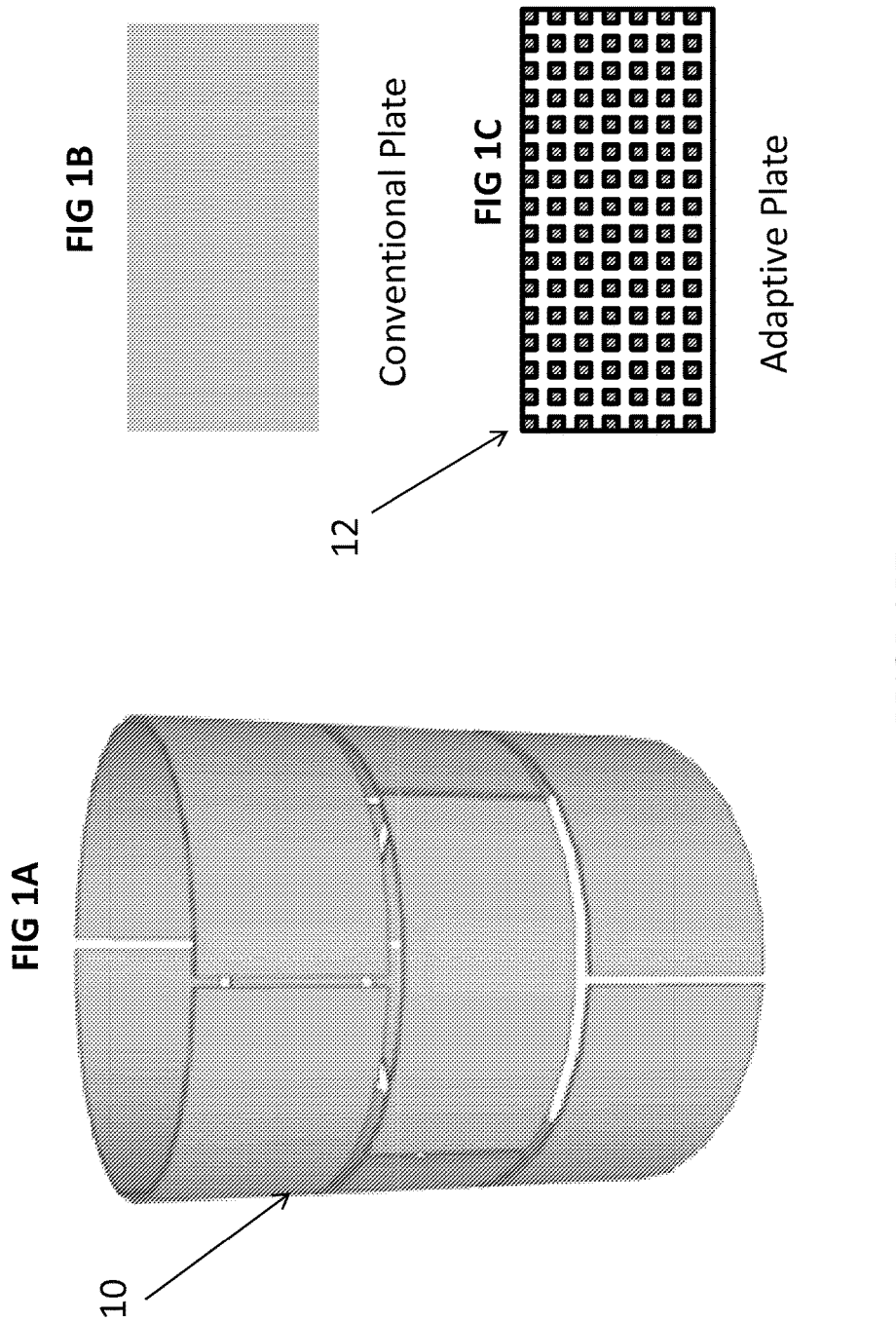
FIG. 1A illustrates one embodiment of a ECVT and AECVT sensor.
FIG. 1B illustrates one embodiment of a sensor capacitance plate of the sensor.
FIG. 1C illustrates one embodiment of a capacitance plate of an AECVT sensor having multiple segments.

FIG. 1A illustrates one embodiment of an ECVT or AECVT sensor. FIG. 1B illustrates one embodiment of a sensor capacitance plate of the sensor. FIG. 1C illustrates one embodiment of a capacitance plate of an AECVT sensor having multiple segments. In one embodiment, a conventional ECVT sensor is configured using 12 plates. FIGS. 1b and 1C illustrate a AECVT plate compared to a conventional ECVT plate.

Figure 2:
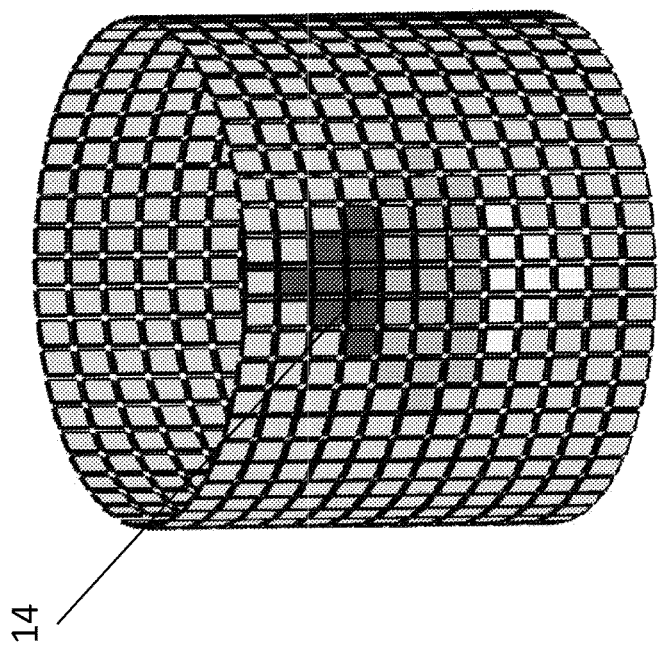
FIG. 2 illustrates one embodiment of AECVT sensor.

FIG. 2 illustrates one embodiment of a full AECVT sensor 14 having plates with multiple segments (e.g., electrodes) where each segment can be activated with different voltage levels. Synthetic plates may be formed by combining the aggregate response of all activated segments.

Figure 3:
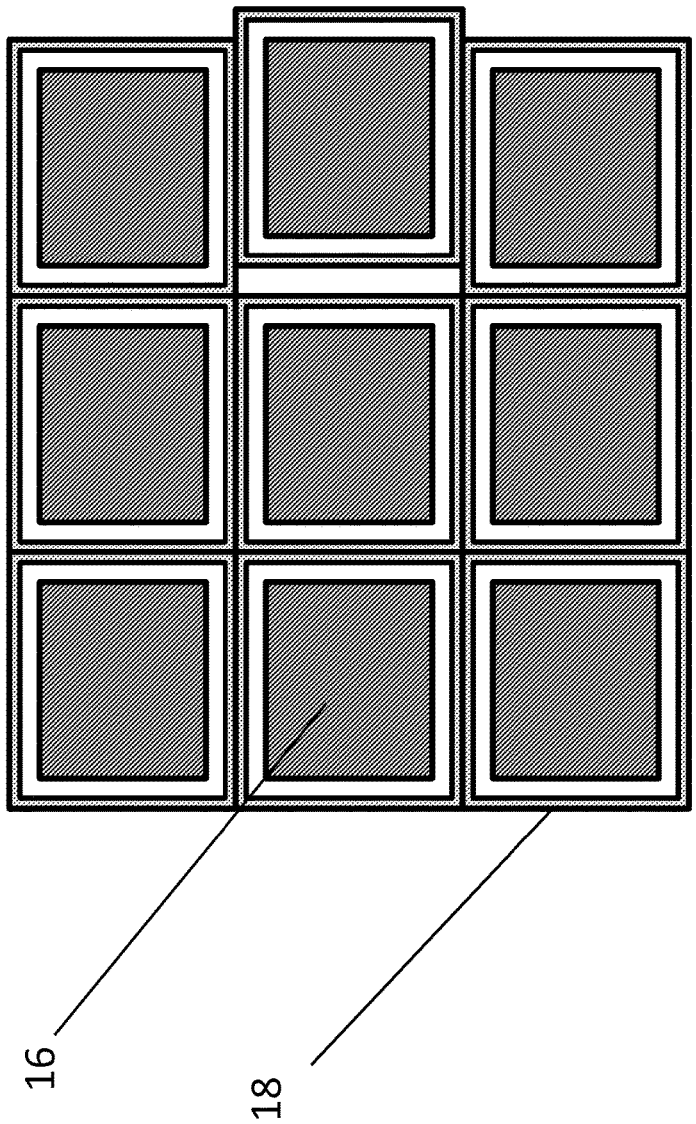
FIG. 3 illustrates one embodiment of an ACECVT sensor plate with each segment surrounded by active control guards.

FIG. 3 illustrates one embodiment of an AECVT sensor plate where each plate segment 16 is surrounded by an active control guard 18, (e.g., an active control guard ring). In another embodiment of the invention, an ECVT plate is surrounded by an active control guard ring. The active control guard ring of each segment or plate is preferably activated with different voltage levels accordingly to the voltage level of an enclosed segment or plate. Different guard activation levels on the active control guards are used to control the charge distribution on the sender/receiver segments or plates. In one embodiment, the active control guards are metal plates that may or may not be the same material as the sender/receiver plate/segments. In another embodiment they may be made from resistive or dissipative material. These active control guards (or active control segments) are used in the present invention to control charge distribution on the plates and therefore control the sensitivity matrix of the sensor.

In the preferred embodiment, active control guards affect charge distribution on both sender and receiver plates at the same time. When they are closer to either plate their effect there is greater. Obtaining desired charge distribution on both plates is a design matter that relates to guard activation patterns. One way is through the basis functions described herein where each guard effect is recorded on both sender and receiver plates. A collection of guards are then activated with a specific activation pattern. The total effect of the pattern on sender and receiver plates is equal to the sum of guards when activated independently.

FIG. 4 illustrates one example circuit embodiment for single excitation and receiver channels to measure the capacitance of adaptive sensor segments for single capacitance measurements in isolation of active control guard excitation. This building block can be used with other circuit components (e.g., like FIG. 2) to form a full system to measure multiple capacitance values of an AECVT sensor. This building block features: 1) Isolation amplifier 20 to drive active control guard electrodes and to isolate them from changing current measured from AECVT segments by providing a separate current return path (e.g., this means measured current that represents capacitance between capacitance electrodes will remain the same regardless of how active guards are activated. Since active guards current is isolated from the measured current, measured current will not change.); 2) Each segment is preferably activated with different voltage levels depending on segment attenuators and each active control guard is preferably activated with a different voltage depending on guard attenuators 22; 3) A separate return current path 24 for active control guards that leads back to the isolation amplifier; 4) Active control guards' receiver plates or segments that serve as return path for current from active control guards sender plates. Active control guards are composed of capacitance plates and have sender and receiver plates. They are distinct from sensor sender and receiver plates as current from active guards does not pass through measuring circuits. Instead, it is diverted back to isolation circuit. This is accomplished by constructing receiver guard plates that serve as independent paths for current. FIG. 4 shows control guard receiver segments 26 that serve as return path for current from control guards. Guard current here is diverted from measuring circuit by isolating amplifier; and 5) After all excitation segments are addressed, receiver signals are all added into one signal that represents a synthetic pair of capacitance plates.

FIG. 5 illustrates one embodiment of the invention having guards segmented 28 around each AECVT segment. In another embodiment, these guard segments can also be placed around an ECVT plate. Different guard excitations may be used to tilt the sensitivity map of the enclosed plate or segment.

FIGS. 6A-D illustrate examples of the change of charge distribution on AECVT plate segments by controlling the active control guard excitation around the plate segments. FIG. 6A is for a cylindrical AECVT sensor with no active guards. FIG. 6B is for a cylindrical AECVT sensor with active guards around sensor sender plates. FIG. 6C is for charge distribution with FIG. 6D activation. Here, charge distribution is not homogenous. FIG. 6D shows charge distribution on sender plates with active guards activated and configured to homogenous charge distribution on sender segments/plates. The figures show an ability of control charge distribution on sender plate by changing the activation of active guards.

FIGS. 7A-C illustrate examples where the sensitivity of a plate combination is changed by active control guard excitation while the capacitance value of the plate combination is maintained due to no change in the geometry of plates with respect to each other. Here, the sensitivity distribution map is altered in each case by solely changing the active control guards' excitation.

The sensitivity distribution map is calculated in each case using the enforced charge approach. FIG. 7A illustrates conventional activation of sender plates without active guards. The figure shows a non-uniform sensitivity distribution. FIG. 7B illustrates the activation of a sensor with active guards with tapered activation surrounding the sender plate. Here, the charge distribution on the sender plate is homogenous and the sensitivity map is also homogenous. FIG. 7C illustrates the activation of a sensor with guard activation on three sides of the sender plate. Here, the sensitivity distribution is homogenous except at the side where active guards are not used. This figure illustrates the ability to control sensitivity distribution through different activation of control guards. (The three 3D boxes of FIG. 7 illustrate the sensitivity maps for each of FIGS. 7A, 7B, and 7C respectively.)

FIG. 8 is an example of changing sensitivity by rearrangement of segment/guard activation. The preservation of geometry eliminates the need for data normalization. FIG. 8A illustrates an example of a 2D depiction of a parallel plate capacitance combination showing various segment and guard excitations. Capacitance for both distributions is the same. Capacitance for both distributions is the same. FIG. 8B illustrates a 2D profile of parallel plate geometry.

Rearrangement of segment and active control guard excitation changes the sensitivity map between the parallel plates while maintaining the mutual capacitance between them since the geometry is kept fixed. For example, because the measured capacitance between sender and receiver plates is related to the change in charge relative to change in activation voltage, if segments in FIG. 8 are maintained at the same average activation voltage and measured capacitance or charge is also unchanged (due to maintaining fixed plate geometry), then sensitivity can be changed by rearranging activation levels across segments. In this case, the rearranged sender activation will not change measured capacitance (as physical plate geometry is still the same and average activation voltage is maintained). However, sensitivity will change as activation distribution across the plate is changing.

This flexible arrangement, allowing for a change in the sensitivity map while maintaining the inter-plate geometry fixed in AECVT sensors, enables rationometric calibration. Rationometric calibration is based on obtaining different sensitivity maps from plate combinations that have similar capacitance values in a homogenous medium. For the example above, the capacitance measurement is the same for different sender voltage activation levels and the sensitivity is changing as a function of activation distribution on sender segments. Rationometric calibration can be achieved by satisfying those two conditions and is performed by recording the difference between different plate combinations of geometrically similar capacitance measurements in a homogenous medium. The sensor here is calibrated for the difference between measured capacitance and not the absolute value of each. In a homogenous medium, all plate combinations will provide similar capacitance measurements when they have similar geometry. When the medium is not homogenous due to flow conditions, the difference between capacitance measurements is used to reconstruct an image. In conventional ECVT, the normalized capacitance of each independent measurement is used to construct an image. Rationometric calibration is different in that it uses the difference between measurements and not the normalized or absolute values. This Rationometric calibration is valuable since it does not require the sensor to be calibrated with the flow material. It will measure the difference in the capacitance between all plates regardless of flow material. This means the sensor can be operated as plug and play without conventional calibration with flow material. The example in FIG. 8 can be extended to any shape or geometry of ECVT or AECVT sensors.

Rationometric reconstruction eliminates the need to calibrate the sensor with flow material before using it for measurements. For example, plate pairs with similar capacitance response in a homogeneous medium are used to record changes in their capacitance related to flow variation. Rationometric reconstruction uses the difference between those values to reconstruct a flow distribution profile.

In one example embodiment, rationometric reconstruction can be accomplished by:
1) activating a first plate formed from a first combination of electrodes and active control segments;
2) measuring a first capacitance between the first plate and a first receiver plate;
3) activating a second plate formed from a second combination of electrodes and active control segments, wherein the second plates has a similar geometry or effective geometry to the first plate when activated with a homogeneous medium;
4) measuring a second capacitance between the second plate and a second receiver plate;
5) recording the difference between the first and second capacitances; and
6) using the difference for analysis of flow through the sensor.

FIG. 9 is an example of changing sensitivity by rearrangement of segment/guard activation (or use of different plate combinations). The preservation of equivalent geometry eliminates the need for data normalization. FIG. 9A illustrates an example of a 2D depiction of a parallel plate capacitance combination showing various segment and guard excitations for various plate combinations. Capacitance for both distributions is the same. A specific activation of sender/receiver electrodes 30 and a specific activation of related guards 32 is rearranged as in 34 to yield similar capacitance but different sensitivity distribution between sender and receiver electrodes. FIG. 9B illustrates a 2D profile of parallel plate geometry in which sender and receiver plates 36 are configured to each case in FIG. 9A. Here, an "effective" geometry is preserved by exciting segments and active control guards in both geometries to yield a similar measured signal (i.e. current through measuring circuit) for a homogenous dielectric distribution in both cases of different geometry of the parallel plate setting. Such arrangement, allowing for a change on the sensitivity map while maintaining "effective geometry" in AECVT sensors, enables the use of rationometric calibration when interactive charge levels are preserved.

FIG. 10 shows a reconfiguration of the excitation pattern used in the active control guards in order to maintain close to homogenous charge distribution on receiver and sender capacitance plates when a phantom 42 of relatively low dielectric constant is introduced in the imaging domain 40. Here, the sensitivity 44 only changes very near the location of the phantom, and the sensitivity map is still focused otherwise 46.

FIG. 10A is for the sensitivity map between opposite plate configuration in a homogenous domain. Guards are activated here to provide a homogenous sensitivity map. FIG. 10B is for the sensitivity map of a domain with a phantom. Here, the phantom is an object with a dielectric value (3 in this case) different than the background (1 in this case). The guards are activated such that the sensitivity map is only affected in the region where the phantom exists. The significance of this example is that it shows that active guards can be used to focus the sensitivity map and restrict the change to the region where a change in dielectric distribution happened. This is significant because it establishes a near linear relation between sensitivity map and phantom location (dielectric distribution) when active guards are activated properly. Conventional ECVT and AECVT sensors have a nonlinear relation between sensitivity map and dielectric distribution, which complicates image reconstruction and limits image resolution of reconstructed image. Active guards in this example can be used to relax this nonlinearity and potentially provide higher resolution. Reference numeral 40 refers to the homogenous domain referred to and reference numeral 42 to the phantom.

Excitation patterns are used to counter polarization introduced by the phantom of flow material. This is achieved by first assessing the level of polarization by conducting a first scan of the domain with only capacitance sensors (no active guards). Then, the second step is to use the measured capacitance to figure polarization of each sensor plate. Typically, the higher the measured capacitance in the first step the higher the polarization. Then thirdly, a desired charge distribution is determined to counter measured polarization. In the fourth step, guards are activated to provide this desired charge distribution on sensor plates. The result of all those steps is to establish a close to linear relation between sensitivity map and dielectric distribution in the imaging domain.

FIG. 11 shows a reconfiguration of the excitation pattern used in the active control guards in order to produce a tapered charge distribution on receiver and sender capacitance plates when a phantom 48 of relatively high dielectric constant is introduced in the imaging domain 40. Here, the sensitivity 50 only changes very near the location of the phantom, and the sensitivity map is still focused otherwise 52.

FIG. 11A illustrates a uniform sensitivity distribution between opposite plates in a capacitance sensor with active control guards. FIG. 11B illustrates a highly polarizing phantom (dielectric value is 81) in the imaging domain. Here, the phantom is located near the edge of the sender capacitance plate. A tapered charge distribution is required to counter the high polarization of charges introduced by the phantom. This desired charge distribution is depicted on the plate where right edge indicates high charge distribution and the left edge indicates low charge distribution. FIG. 11C depicts the sensitivity distribution after the desired activation on active control guards is applied. The sensitivity here mainly changes at the location where the phantom is located. The sensitivity map is related in this case to the phantom location in a near linear relation. Reference numeral 48 here refers to a phantom with high dielectric constant. The tapered charge distribution is shown on the surface of sender plate. The activation of active control guards is similar to the process described in the preceding paragraph. A phantom is an object with a dielectric value different than the background. It is desirable to establish a near linear relation between sensitivity map and dielectric distribution. This linear relation will enable faster and better image reconstruction.

What is claimed is:

1. A system for generating a three-dimensional tomograph of a vessel interior or other object, the system comprising:
a three-dimensional capacitance sensor device comprising a plurality of electrodes for placement around the vessel or the object, wherein the three-dimensional capacitance sensor device is adapted to provide electric field distribution and sensor sensitivity in three geometric dimensions;
data acquisition electronics in communication with the three-dimensional capacitance sensor device for receiving input data from the plurality of electrodes of the three-dimensional capacitance sensor device;
a plurality of active control segments placed around the plurality of the electrodes, wherein each of the plurality of active control segments are electrically isolated from the plurality of electrodes;
an isolation circuit connected to each of the plurality of active control segments comprising an independent path for currents that is electrically isolated from current on the plurality of electrodes;
a processing system in communication with the data acquisition electronics, the processing system programmed with instructions for executing on the processing system to reconstruct a three-dimensional volume-image from the input data collected by the data acquisition electronics;
wherein the system is configured to allow activation of each active control segment individually and wherein the system is configured to activate the active control segments with a specific activation pattern.

2. A system according to claim 1, wherein any pair of electrodes can act as a sender capacitance plate and a receiver capacitance plate and wherein activation of an active control segment around the sender capacitance plate modifies a charge distribution on the sender or receiver capacitance plates for controlling sensitivity distribution without affecting a capacitance between the sender capacitance plate and the receiver capacitance plate.

3. A system according to claim 1, wherein the system is configured to activate the plurality of active control segments in a predetermined excitation pattern for focusing sensitivity of the sensor device.

4. A system according to claim 1, wherein the processing system is programmed with an image reconstruction algorithm and wherein the sensor is an adaptive electrical capacitance volume tomography sensor.

5. A system according to claim 4, wherein the image reconstruction algorithm is adapted to provide real-time imaging of multiphase flow within the vessel.

6. A system according to claim 1, wherein the processing system is programmed to calculate capacitance data from the input data received by the data acquisition electronics.

7. A system according to claim 1, wherein the processing system is programmed with instructions to: 1) activate the plurality of the active control segments independently; and 2) record charge distribution effect of each individual activation on the plurality of the electrodes.

8. A system according to claim 1, wherein the three-dimensional capacitance sensor device is any shape or arrangement of electrodes that provides a three-dimensional electric field intensity in three directions with substantially equal strength.

9. A system according to claim 1, further comprising:
a time varying driving signal for use as an excitation signal for the system.

10. A system according to claim 1, wherein the system is configured so that activation of the plurality of active control segments does not change a capacitance between the plurality of electrodes that the plurality of active control segments are placed around.

11. A system according to claim 1, wherein the system is configured so that activation of the plurality of active control segments repels or attracts charges on the plurality of electrodes that the plurality of active control segments are placed around.

12. A system according to claim 1, wherein each active control segment is a metal segment in a ring shape that surrounds an electrode of the sensor.

13. A system according to claim 1, further comprising: means for activating each of the plurality of active control segments; and wherein the system is configured to control a charge distribution on the electrodes by activating the plurality of active control segments with a voltage.

14. A system according to claim 13, wherein the means for activating is an isolation amplifier.

15. A system according to claim 13, further comprising: a plurality of attenuators, one attenuator connected to each of the plurality of active control segments, for controlling the level of activation of each of the active control segments.

16. A system according to claim 1, wherein a total effect of the activation pattern on activated active control segments is equal to the sum of the activated control segments when activated independently.

17. A system according to claim 1 wherein the system is configured to activate the plurality of active control segments to generate near uniform charge distribution on the plurality of electrodes.

18. A system according to claim 1 wherein the system is configured to generate controlled charge distributions of various patterns on the plurality of electrodes for obtaining capacitance measurements and to reduce field singularities in an imaging domain of the sensor.

19. A system according to claim 1, wherein the any combination of electrodes and active control segments can act as a sender capacitance plate wherein the system is configured to modify a charge distribution on the sender capacitance plate to tilt the sensitivity of the sensor toward a predetermined direction.

20. A system according to claim 1, wherein the processing system is programmed with instructions to vary activation of a plurality of active control segments and electrodes to construct geometrically similar combinations of electrodes and active control segments in the sensor.

21. A system according to claim 20, wherein the processing system is programmed with further instructions to electronically switch the activation of different electrode pairs around a near symmetrical geometry.

22. A system according to claim 1, wherein the processing system is programmed with instructions to: 1) record or identify an active control segment pattern required to produce a near uniform charge distribution on a pair of electrodes for a homogeneous dielectric distribution in an imaging domain of the sensor; 2) measure a capacitance between activated electrode pairs for a time-dependent dielectric distribution in the imaging domain of the sensor; and 3) use the measured capacitances to determine a required active control segment pattern for achieving a near linear relation between the sensitivity and dielectric distribution of a time-dependent dielectric distribution in the imaging domain.

23. A system according to claim 1, wherein the processing system is programmed with instructions to use different activation patterns for the plurality of active control segments and plurality of electrodes to form capacitance pairs of electrodes with similar capacitance response to a homogeneous dielectric distribution.

24. A system for generating a three-dimensional tomograph of a vessel interior or other object, the system comprising:
a three-dimensional capacitance sensor device comprising a plurality of electrodes for placement around the vessel or the object, wherein the three-dimensional capacitance sensor device is adapted to provide electric field distribution and sensor sensitivity in three geometric dimensions;
data acquisition electronics in communication with the three-dimensional capacitance sensor device for receiving input data from the plurality of electrodes of the three-dimensional capacitance sensor device;
a plurality of active control segments placed around the plurality of the electrodes; wherein each of the plurality of active control segments are electrically isolated from the plurality of electrodes;
an isolation circuit connected to each of the plurality of active control segments comprising an independent path for currents that is electrically isolated from current on the plurality of electrodes;
a processing system in communication with the data acquisition electronics, the processing system programmed with instructions for executing on the processing system to: 1) activate a plurality of active control segments and electrodes in a predetermined pattern; 2) reconstruct a three-dimensional volume-image from the input data collected by the data acquisition electronics; and
wherein the system is configured to allow activation of each active control segment individually and wherein the system is configured to activate the active control segments with a specific activation pattern.

25. A method for generating a three-dimensional tomograph of a vessel interior or other object, the method comprising the steps of:
providing a three-dimensional capacitance sensor device comprising a plurality of electrodes for placement around the vessel or the object, wherein the three-dimensional capacitance sensor device is adapted to provide electric field distribution and sensor sensitivity in three geometric dimensions;

providing data acquisition electronics in communication with the three-dimensional capacitance sensor device for receiving input data from the plurality of electrodes of the three-dimensional capacitance sensor device;

providing a plurality of active control segments placed around a plurality of the electrodes; wherein each of the plurality of active control segments are electrically isolated from the plurality of electrodes;

providing an isolation circuit connected to each of the plurality of active control segments comprising an independent path for currents that is electrically isolated from current on the plurality of electrodes;

activating a plurality of active control segments and electrodes in a predetermined pattern; and reconstructing a three-dimensional volume-image from the input data collected by the data acquisition electronics.

26. A method according to claim 25, wherein the step of activating the plurality of active control segments in a predetermined excitation pattern focuses sensitivity of the sensor device.

27. A method according to claim 25, further comprising the step of varying activation of a plurality of active control segments and electrodes to construct geometrically similar or electrode pairs or active control segments in the sensor.

28. A method according to claim 25, further comprising the steps of: performing rationometric calibration by: 1) activating a first plate formed from a first combination of electrodes and active control segments; 2) measuring a first capacitance between the first plate and a first receiver plate; 3) activating a second plate formed from a second combination of electrodes and active control segments, wherein the second plate has a similar geometry or effective geometry to the first plate when activated with a homogeneous medium; 4) measuring a second capacitance between the second plate and a second receiver plate; 5) recording a difference between the first and second capacitances; and 6) using the difference for analysis of flow through the sensor.

29. A method according to claim 28, further comprising the step of:

using the recorded difference to reconstruct a flow distribution profile.

* * * * *